United States Patent
Hansen et al.

(10) Patent No.: US 8,209,008 B2
(45) Date of Patent: Jun. 26, 2012

(54) INTERACTIVE AUTOMATIC EXTERNAL DEFIBRILLATOR PROVIDING ATTACHMENT GUIDANCE TO OPERATOR

(75) Inventors: Kim Hansen, Renton, WA (US); Thomas D. Lyster, Bothell, WA (US); Kurt V. Fischer, Lynnwood, WA (US); James Adkins Froman, Issaquah, WA (US); Douglas Michael Denney, Sammamish, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1668 days.

(21) Appl. No.: 10/531,359

(22) PCT Filed: Oct. 13, 2003

(86) PCT No.: PCT/IB03/04501
§ 371 (c)(1),
(2), (4) Date: Apr. 13, 2005

(87) PCT Pub. No.: WO2004/037345
PCT Pub. Date: May 6, 2004

(65) Prior Publication Data
US 2006/0116723 A1    Jun. 1, 2006

Related U.S. Application Data

(60) Provisional application No. 60/420,767, filed on Oct. 23, 2002.

(51) Int. Cl.
*A61N 1/39* (2006.01)
(52) U.S. Cl. .............................. 607/8; 607/5
(58) Field of Classification Search .............. 607/8, 5
See application file for complete search history.

(56) References Cited

U.S. PATENT DOCUMENTS

| | | | |
|---|---|---|---|
| 3,805,795 A | 4/1974 | Denniston et al. | |
| 4,165,749 A | 8/1979 | Cansell | |
| 4,706,680 A | 11/1987 | Keusch et al. | |
| 5,645,571 A * | 7/1997 | Olson et al. | 607/5 |
| 5,700,281 A | 12/1997 | Stolte et al. | |
| 5,797,969 A * | 8/1998 | Olson et al. | 607/5 |
| 6,075,369 A | 6/2000 | Morgan | |
| 6,083,246 A | 7/2000 | Stendahl et al. | |
| 6,201,992 B1 | 3/2001 | Freeman | |
| 6,292,697 B1 | 9/2001 | Roberts | |
| 6,334,070 B1 | 12/2001 | Nova et al. | |
| 6,336,047 B1 | 1/2002 | Thu et al. | |
| 6,356,785 B1 | 3/2002 | Gliner et al. | |
| 6,697,671 B1 * | 2/2004 | Nova et al. | 607/5 |
| 7,069,074 B2 * | 6/2006 | Covey et al. | 607/5 |
| 7,310,553 B2 * | 12/2007 | Freeman | 607/5 |
| 2003/0055478 A1 | 3/2003 | Griesser et al. | |

FOREIGN PATENT DOCUMENTS

| | | |
|---|---|---|
| EP | 0057561 B1 | 4/1986 |
| WO | WO 0156652 A1 | 8/2001 |

* cited by examiner

*Primary Examiner* — Michael Kahelin
(74) *Attorney, Agent, or Firm* — W. Brinton Yorks, Jr.

(57) ABSTRACT

A method for operating an automatic external defibrillator (AED) prompts an operator about proper operation of the automatic external defibrillator and placement of the electrodes to ensure rapid and proper operation. Depending upon a state of a pad storage compartment, upon activation the AED issues an initial prompt, pauses after the initial prompt and then issues a second prompt. The AED also determines whether the pads have been removed from a liner and if so, issues a pad application prompt. The AED next determines whether both pads have been placed and if so, analyzes an impedance signal and if the impedance signal is erratic, issues a pad correction prompt. The AED also issues the pad correction prompt if the pads are removed from the liner but never go on the patient.

4 Claims, 1 Drawing Sheet

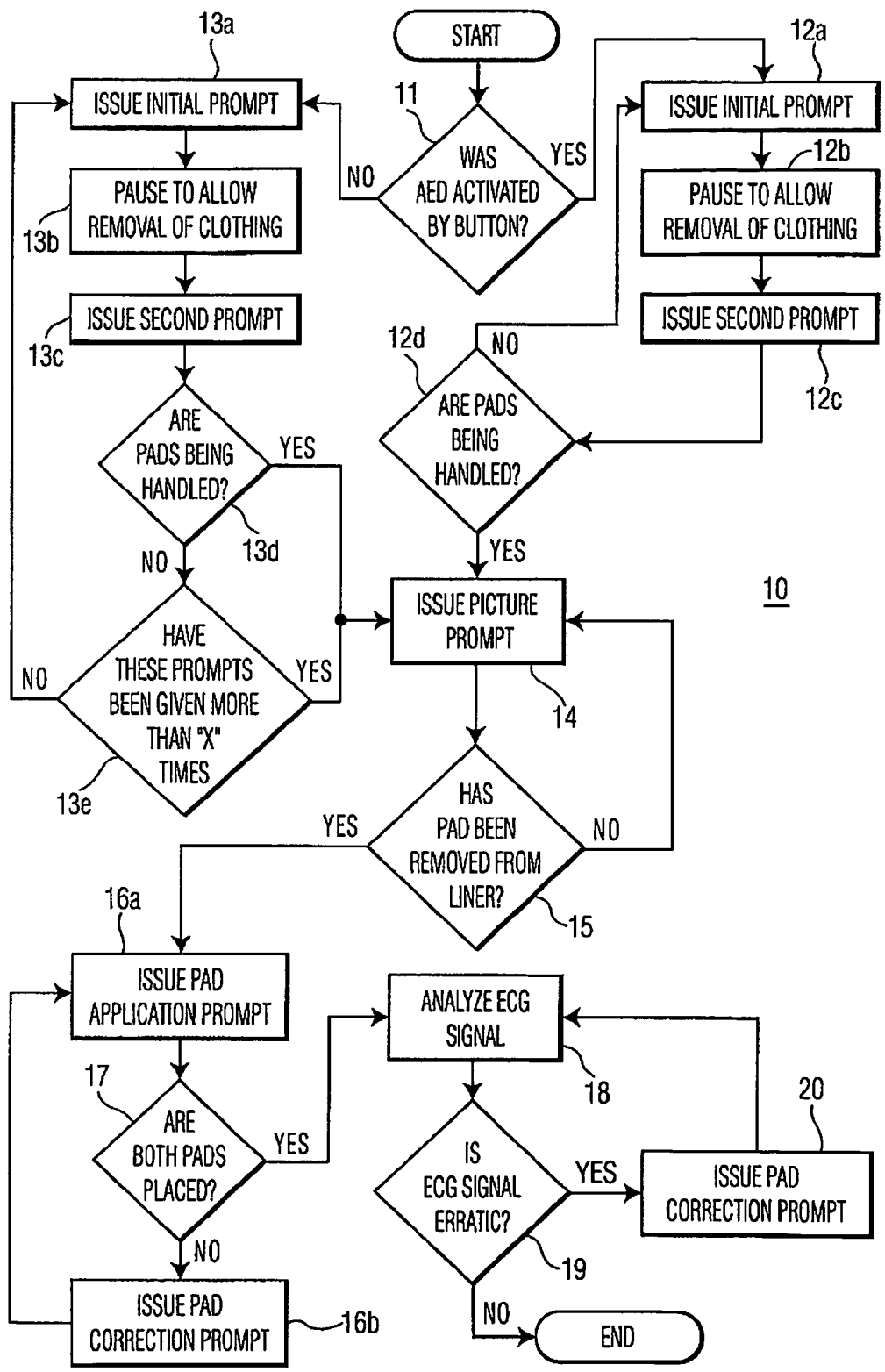

INTERACTIVE AUTOMATIC EXTERNAL DEFIBRILLATOR PROVIDING ATTACHMENT GUIDANCE TO OPERATOR

CROSS REFERENCE TO RELATED APPLICATION

This application claims the benefit of U.S. provisional application Ser. No. 60/420,767 filed Oct. 23, 2002, which is incorporated herein by reference.

The present invention is directed to methods and apparatuses for interacting with operators of automatic external defibrillators, and more particularly to a method and apparatus for interacting with an operator of an automatic defibrillator to ensure proper operation.

Existing Automatic External Defibrillators (AEDs) deliver a series of voice prompts when activated, which include prompts to deploy electrodes from their container, attach the electrodes to the patient, and plug in the pads of the connector at a specified location. However, existing AEDs do not sense intermediate steps in this process nor offer specific guidance during pad deployment and attachment. Thus, the most skill-intensive steps in the operation of the AED must be performed "open-loop" by the operator. These deployment steps are the most prone to operator error.

A persistent problem with prior AEDs was that following initial "apply pads" prompts, operators were required to perform a detailed series of skilled operations in order to attach the AED and its electrode pads to the patient. The operator has to: assure that emergency medical services are called, remove clothing from the patient's chest, find a package of AED electrodes, open the bag and remove the electrodes, peel each electrode from a backing, place each pad in a proper location on the patient's chest, assure that the electrodes are adhered correctly, and plug in the lead wires from the pads to the AED (in some devices). Existing AEDs could next sense if the pads were connected to appropriate impedance and proceed to perform ECG analysis. However, errors in the intervening attachment steps often resulted in inconsistent or poor pad placement accuracy, or in a wide variation in the time taken to perform all steps due to operator confusion. This situation is exacerbated by the extreme stress under which an untrained operator is typically performing these tasks. Moreover, most potential operators of an AED are not normally trained to perform the requisite tasks under these high stress situations.

The present invention is therefore directed to the problem of developing a method and apparatus for facilitating the proper operation of an AED, and in particular facilitating proper deployment of the pads.

The present invention solves these and other problems by providing, inter alia, an Automatic External Defibrillator (AED) that interacts with the operator during the initial phases of a rescue or operation. In particular, according to one exemplary embodiment of the AED of the present invention, the embodiment senses various progressive states of pad deployment and attachment, and provides specific operator guidance (e.g., one or more prompts) based upon this sensed information.

According to an exemplary embodiment of a method for operating an AED, various device operating conditions are determined following device activation. Knowledge of the operating conditions of the device allows specialized instructions to be delivered during sequential phases of electrode pad deployment and placement on the patient by the operator. This results in more accurate pads placement and more consistent time intervals to complete these steps than previous devices.

FIG. 1 depicts an exemplary embodiment of a method for interacting with an operator of an Automatic External Defibrillator according to one aspect of the present invention.

It is worthy to note that any reference herein to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

Referring to FIG. 1, shown therein is a flowchart of an exemplary embodiment 10 of a method for operating an Automatic External Defibrillator (AED) according to one aspect of the present invention. The AED may be activated by either pressing an ON/OFF button or by pulling a lever that removes a protective cover. Thus, the AED must first determine the activation state of itself. This can be accomplished by noting the state in which the ON/OFF switch or button lies, or determining whether a cover is being removed, in which case a contact can be opened or closed, which can easily be sensed. Alternatively, the AED can sense a change in the state of the ON/OFF button.[KH1]

If the AED is turned ON by pressing the button (determination made in element 11), the AED issues an initial prompt (element 12a), in which the operator is prompted to (or similar words to this effect):

1. "BEGIN BY REMOVING ALL CLOTHING FROM THE PATIENT'S CHEST."
2. "CUT CLOTHING IF NEEDED."
3. "CALL EMERGENCY MEDICAL SERVICES."[KH2]
   This final instruction may be included in some embodiments and may be left out in others.

Alternatively, the final instruction may be in the form of a reminder to simply be sure emergency services have been called.

After a pause timed to permit clothing removal (element 12b), the AED issues a second prompt (element 12c), in which the operator is instructed (or words similar to these):

1. "WHEN A PATIENT'S CHEST IS BARE, REMOVE PROTECTIVE COVER AND TAKE OUT WHITE ADHESIVE PADS."

This prompt is repeated at predetermined intervals (e.g., every 5 seconds) until the AED senses that the protective cover has been removed and that the pads are being handled (determination made in element 12d). If on the other hand, the AED is activated by pulling a handle and removing a cover (i.e., the button is not used to activate the AED), the AED will repeat the initial prompt (element 13a), pause (element 13b), and then issue the second prompt (element 13c). Then the AED will determine if the pads are being handled (element 13d). If not, the AED will repeat elements 13a-c for a predetermined number of times (e.g., x=3) and then move on to the next step in the pads deployment procedure, i.e., element 14. In this case, it is assumed that the operator has removed the pads from their container but the AED's method for detecting this event was not able to do so successfully.

Upon detecting pad handling, or after a pre-determined amount of time has elapsed, the AED then issues a picture prompt (element 14), in which the operator is instructed (or with similar words to these):

1. "LOOK CAREFULLY AT THE PICTURES ON THE WHITE ADHESIVE PADS. PEEL ONE PAD FROM THE YELLOW PLASTIC LINER."

This prompt 14 repeats until the AED senses that a pad has been removed from the liner (element 15). While on the liner, the pads are in electrical contact with one-another and the AED impedance detection circuitry senses this state. An alternative is to sense each pad's contact state individually using two wires to each pad and a contact-completion detector. This prompt 14 is specifically designed to stop an operator and bring attention to the purpose of the icons that are printed on the pads. Lacking this interruption, naïve users tend to intuitively understand that the pads are to be adhered to the patient, but do not pick up on the fact that the pictures on the pads have significance. Thus, operators tend to locate the pads in random fashion, favoring the ineffective side-by-side positioning seen on television shows.

Once a pad has been removed from the liner by the operator, the AED issues a pad application prompt (element 16*a*), in which the operator is instructed (or with words to this effect):

1. "PLACE PAD EXACTLY AS SHOWN IN THE PICTURE."
2. "PRESS FIRMLY TO PATIENT'S BARE SKIN."
3. "WHEN THE FIRST PAD IS IN PLACE, LOOK CAREFULLY AT THE PICTURE ON THE SECOND PAD."
4. "PEEL THE SECOND PAD FROM THE YELLOW PLASTIC LINER."
5. "PLACE PAD EXACTLY AS SHOWN IN THE PICTURE."
6. "PRESS FIRMLY TO PATIENT'S BARE SKIN."

Again the prompt sequence repeats as needed until the AED senses that both pads are placed (element 17). Rapid pad attachment by an operator causes intermediate steps to be skipped or abbreviated. When both pads are in place, the AED proceeds to analyze the patient's ECG signal (element 18). Here again, by use of specific instructions to locate the pads as shown in the pictures, operators are provided information crucial to successful placement.

If the pad contact is erratic (determination made in element 19) or otherwise unacceptable for ECG analysis, the AED issues a pad correction prompt (element 20), in which the operator is instructed (or with words similar to these):

1. "PRESS PADS FIRMLY TO PATIENT'S BARE SKIN."
2. "MAKE SURE THAT THE YELLOW PLASTIC LINER IS COMPLETELY REMOVED FROM BOTH PADS."
3. "PLACE PAD EXACTLY AS SHOWN IN THE PICTURE."
4. "PADS MUST NOT BE TOUCHING CLOTHING OR EACH OTHER."

Testing has shown that these steps markedly improve operator success.

The AED also issues the pad correction prompt if the pads are removed from the liner but never go on the patient (element 16*b*), as this would signal that either one of the two pads are broken or that the operator has done something like forgotten to remove the plastic liner or has placed one or both pads on clothing.[KH3]

In summary, the AED of the present invention provides several features to ensure rapid and correct operation. For example, the AED includes a provision for sensing and prompting steps between device turn-on and pad attachment, thus breaking down a complex skill requirement into several simple ones. Furthermore, two different prompt sequences are employed depending upon how the AED is activated (e.g., by button or handle). Additionally, the AED includes a provision for an operator prompt to call emergency medical services, which can be forgotten in the panic of the moment in which an AED is likely to be employed. Moreover, the AED includes an operator prompt to remove cover and take out pads. The AED also includes the capability to sense when pads are being handled, even when the pads are still on their liner, and to issue associated prompts for the next step. This is a key prompt for placement accuracy, without it AEDs have markedly poor performance. Still further, the AED includes the capability to sense when one pad has been removed from its liner, and to issue appropriate prompts for what to do next. Yet, the AED also includes a prompt to place the pads as shown in pictures on the pads. This picture prompt one is very effective and valuable, as otherwise the pads are often placed in an incorrect or ineffective position. The AED also includes prompts providing visual differentiation to elements that must be handled by the operator, such as: "White adhesive pads," "yellow plastic liner," and pictures noted on pads. In addition, the AED includes error correction prompts if pad contact is erratic that is specific to correcting certain typical problems, such as pads touching each other, failure to remove or release the liner, or pads being placed on clothing. Other features of the exemplary AED are evident from the description above.

Although various embodiments are specifically illustrated and described herein, it will be appreciated that modifications and variations of the invention are covered by the above teachings and are within the purview of the appended claims without departing from the spirit and intended scope of the invention. For example, specific operator instructions are provided, however, similar instructions conveying similar information may also be used. Furthermore, this example should not be interpreted to limit the modifications and variations of the invention covered by the claims, but is merely illustrative of one possible variation.

The invention claimed is:

1. A method for guiding an operator of an automatic external defibrillator in pad placement on a subject comprising:
    prompting an operator to conduct a pad placement action;
    sensing whether the pads are in proper contact with the subject and, if they are not;
    following sensing, issuing a pad correction prompt to remove a pad liner.

2. A method for guiding an operator of an automatic external defibrillator in pad placement on a subject comprising:
    prompting an operator to conduct a pad placement action;
    sensing whether the pads are in proper contact with the subject and, if they are not;
    following sensing, issuing a pad correction prompt that the pads must not be touching each other.

3. The method according to claim 1, further comprising repeating a prompt until the defibrillator senses that the operator has conducted the prompted action.

4. The method according to claim 2, further comprising repeating a prompt until the defibrillator senses that the operator has conducted the prompted action.

* * * * *